(12) United States Patent
Houser et al.

(10) Patent No.: US 7,854,735 B2
(45) Date of Patent: Dec. 21, 2010

(54) ENERGY-BASED MEDICAL TREATMENT SYSTEM AND METHOD

(75) Inventors: Kevin L. Houser, Springboro, OH (US); Sarah A. Noschang, Mason, OH (US); Jorge N. Gutierrez, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1077 days.

(21) Appl. No.: 11/355,463

(22) Filed: Feb. 16, 2006

(65) Prior Publication Data

US 2007/0191828 A1 Aug. 16, 2007

(51) Int. Cl.
*A61B 18/18* (2006.01)

(52) U.S. Cl. .............. 606/40; 606/49; 606/50; 606/51; 606/52; 606/205

(58) Field of Classification Search ............ 606/32–34, 606/49, 50–52, 169, 205–209
See application file for complete search history.

(56) References Cited

U.S. PATENT DOCUMENTS

| | | | |
|---|---|---|---|
| 4,246,490 A | 1/1981 | Keramati et al. |
| 4,371,816 A | 2/1983 | Wieser |
| 4,452,473 A | 6/1984 | Ruschke |
| 4,660,573 A | 4/1987 | Brumbach |
| 4,696,667 A | 9/1987 | Masch |
| 4,731,545 A | 3/1988 | Lerner et al. |
| 4,979,952 A | 12/1990 | Kubota et al. |
| 5,057,119 A | 10/1991 | Clark et al. |
| 5,059,210 A | 10/1991 | Clark et al. |
| 5,156,613 A | 10/1992 | Sawyer |
| 5,167,725 A | 12/1992 | Clark et al. |
| 5,205,817 A | 4/1993 | Idemoto et al. |

(Continued)

FOREIGN PATENT DOCUMENTS

CN 1610526 4/2005

(Continued)

OTHER PUBLICATIONS

International Search Report issued regarding International Application No. PCT/US07/01705 (Nov. 1, 2007).
CN, Office Action, Chinese Application No. 200680045032.7, 6 pages (Aug. 21, 2009).
CN, Office Action, Chinese Application No. 200680045032.7, 6 pages (May 12, 2010).

(Continued)

*Primary Examiner*—Linda C Dvorak
*Assistant Examiner*—Amanda Scott
(74) *Attorney, Agent, or Firm*—Verne F. Kreger, Jr.

(57) ABSTRACT

A method for medical treatment includes beginning coagulating patient tissue using an energy-based clamp coagulator, determining the clamping force, and measuring the acoustic impedance of the patient tissue. The method also includes compensating the measured acoustic impedance for clamp pressure and monitoring the coagulation using at least the compensated measured acoustic impedance. A first medical treatment system includes an energy-based clamp coagulator, an acoustic-impedance measurer, and a force measurer. A second system includes an energy-based clamp coagulator having a clamping member which includes, or is adapted to function as, an electrical-impedance-measuring electrode for measuring an electrical impedance of the clamped patient tissue. A third system includes an energy-based clamp coagulator having a clamping member which includes, or is adapted to function as, a temperature sensor for measuring a temperature of the clamped patient tissue.

18 Claims, 4 Drawing Sheets

U.S. PATENT DOCUMENTS

| | | | |
|---|---|---|---|
| 5,209,776 A | 5/1993 | Bass et al. | |
| 5,242,385 A | 9/1993 | Strukel | |
| 5,261,922 A | 11/1993 | Hood | |
| 5,263,957 A | 11/1993 | Davison | |
| 5,289,436 A | 2/1994 | Terhune | |
| 5,306,280 A | 4/1994 | Bregen et al. | |
| 5,318,570 A | 6/1994 | Hood et al. | |
| 5,322,055 A | 6/1994 | Davison et al. | |
| 5,324,297 A | 6/1994 | Hood et al. | |
| 5,324,299 A | 6/1994 | Davison et al. | |
| 5,342,292 A | 8/1994 | Nita et al. | |
| 5,372,585 A | 12/1994 | Tiefenbrun et al. | |
| 5,383,883 A | 1/1995 | Wilk et al. | |
| 5,520,633 A | 5/1996 | Costin | |
| 5,647,851 A | 7/1997 | Pokras | |
| 5,735,875 A | 4/1998 | Bonutti et al. | |
| 5,807,310 A | 9/1998 | Hood | |
| 5,810,869 A | 9/1998 | Kaplan et al. | |
| 5,836,897 A | 11/1998 | Sakurai et al. | |
| 5,843,109 A | 12/1998 | Mehta et al. | |
| 5,853,290 A | 12/1998 | Winston | |
| 5,893,835 A | 4/1999 | Witt et al. | |
| 5,893,880 A | 4/1999 | Egan et al. | |
| 5,895,412 A | 4/1999 | Tucker | |
| 5,897,569 A | 4/1999 | Kellogg et al. | |
| 5,910,150 A | 6/1999 | Saadat | |
| 5,935,143 A | 8/1999 | Hood | |
| 5,941,887 A | 8/1999 | Steen et al. | |
| 5,957,943 A | 9/1999 | Vaitekunas | |
| 5,989,275 A | 11/1999 | Estabrook et al. | |
| 6,004,335 A * | 12/1999 | Vaitekunas et al. | 606/169 |
| 6,033,375 A | 3/2000 | Brumbach | |
| 6,051,010 A | 4/2000 | DiMatteo et al. | |
| 6,053,906 A * | 4/2000 | Honda et al. | 606/1 |
| 6,063,098 A | 5/2000 | Houser et al. | |
| 6,068,647 A | 5/2000 | Witt et al. | |
| 6,206,877 B1 | 3/2001 | Kese et al. | |
| 6,217,591 B1 | 4/2001 | Egan et al. | |
| 6,270,471 B1 | 8/2001 | Hechel et al. | |
| 6,283,981 B1 | 9/2001 | Beaupre | |
| 6,325,811 B1 | 12/2001 | Messerly | |
| 6,352,532 B1 * | 3/2002 | Kramer et al. | 606/41 |
| 6,409,743 B1 | 6/2002 | Fenton, Jr. | |
| 6,436,114 B1 | 8/2002 | Novak et al. | |
| 6,458,142 B1 * | 10/2002 | Faller et al. | 606/169 |
| 6,491,708 B2 | 12/2002 | Madan et al. | |
| 6,526,976 B1 | 3/2003 | Baran | |
| 6,561,983 B2 | 5/2003 | Cronin et al. | |
| 6,562,059 B2 | 5/2003 | Edwards et al. | |
| 6,616,450 B2 | 9/2003 | Mossle et al. | |
| 6,623,444 B2 | 9/2003 | Babaev | |
| 6,633,234 B2 | 10/2003 | Wiener et al. | |
| 6,679,899 B2 | 1/2004 | Wiener et al. | |
| 6,689,086 B1 | 2/2004 | Nita et al. | |
| 6,695,782 B2 | 2/2004 | Ranucci et al. | |
| 6,699,214 B2 | 3/2004 | Gellman | |
| 6,702,761 B1 | 3/2004 | Damadian et al. | |
| 6,761,725 B1 | 7/2004 | Grayzel et al. | |
| 6,887,221 B1 | 5/2005 | Baillargeon et al. | |
| 6,887,252 B1 | 5/2005 | Okada et al. | |
| 6,908,466 B1 | 6/2005 | Bonutti et al. | |
| 7,004,174 B2 | 2/2006 | Eggers et al. | |
| 7,018,354 B2 | 3/2006 | Tazi | |
| 7,335,997 B2 * | 2/2008 | Wiener | 290/1 R |
| 7,338,463 B2 | 3/2008 | Vigil | |
| 7,621,930 B2 | 11/2009 | Houser | |
| 2001/0025184 A1 | 9/2001 | Messerly | |
| 2002/0045860 A1 | 4/2002 | Sussman et al. | |
| 2002/0103438 A1 | 8/2002 | Cronin et al. | |
| 2002/0138037 A1 | 9/2002 | Weimann | |
| 2002/0193798 A1 | 12/2002 | Oh et al. | |
| 2003/0105398 A1 | 6/2003 | Vitek | |
| 2003/0171700 A1 | 9/2003 | Martin et al. | |
| 2004/0006347 A1 | 1/2004 | Sproul | |
| 2004/0039242 A1 | 2/2004 | Tolkoff et al. | |
| 2004/0176686 A1 | 9/2004 | Hare et al. | |
| 2005/0004589 A1 | 1/2005 | Okada et al. | |
| 2005/0038340 A1 | 2/2005 | Vaezy et al. | |
| 2005/0049546 A1 * | 3/2005 | Messerly et al. | 604/22 |
| 2005/0085728 A1 * | 4/2005 | Fukuda | 600/449 |
| 2005/0096679 A1 | 5/2005 | Stulen et al. | |
| 2005/0131401 A1 | 6/2005 | Malecki et al. | |
| 2005/0143726 A1 | 6/2005 | Bortkiewicz | |
| 2006/0257819 A1 | 11/2006 | Johnson | |
| 2007/0060926 A1 | 3/2007 | Escaf | |
| 2007/0129723 A1 | 6/2007 | Houser et al. | |
| 2007/0167965 A1 | 7/2007 | Houser | |
| 2007/0173872 A1 | 7/2007 | Neuenfeldt | |
| 2007/0191712 A1 | 8/2007 | Messerly et al. | |
| 2007/0239028 A1 | 10/2007 | Houser et al. | |
| 2010/0042126 A1 | 2/2010 | Houser et al. | |

FOREIGN PATENT DOCUMENTS

| | | |
|---|---|---|
| EP | 0695535 | 2/1996 |
| EP | 1108394 | 6/2001 |
| EP | 1543854 | 6/2005 |
| EP | 1707131 | 10/2006 |
| WO | 02/076685 | 10/2002 |
| WO | 03/002189 | 1/2003 |
| WO | WO 03/024513 | 3/2003 |
| WO | WO 2004/060447 | 7/2004 |
| WO | 2005/056104 | 6/2005 |
| WO | WO 2005/056104 | 6/2005 |
| WO | 2005/084251 | 9/2005 |

OTHER PUBLICATIONS

CN, Office Action, Chinese Application No. 200710079171.8, 7 pages (Dec. 4, 2009).

CN, Office Action, Chinese Application No. 200780002355.6, 6 pages (Jan. 15, 2010).

PCT, International Search Report, International Application No. PCT/US2007/001705, 2 pages (mailed Nov. 1, 2007; published Jan. 10, 2008.

PCT, International Search Report, International Application No. PCT/US2006/045382, 2 pages (mailed Sep. 14, 2007; published Dec. 6, 2007).

PCT, International Search Report, International Application No. PCT/US2007/001557, 2 pages (mailed Sep. 24, 2007; published Nov. 22, 2007).

PCT, International Search Report, International Application No. PCT/US2006/049641, 2 pages (mailed Sep. 12, 2007; published Nov. 8, 2007).

PCT, International Preliminary Report on Patentability, International Application No. PCT/US2007/001705, 5 pages (Jul. 29, 2008).

PCT, International Preliminary Report on Patentability, International Application No. PCT/US2006/045382, 6 pages (Sep. 14, 2007).

PCT, International Preliminary Report on Patentability, International Application No. PCT/US2007/001557, 5 pages (Jul. 22, 2008).

PCT, International Preliminary Report on Patentability, International Application No. PCT/US2006/049641, 4 pages (Jul. 8, 2008).

EP, Partial European Search Report, European Application No. 07250615.7, 4 pages (May 31, 2007).

EP, European Search Report, European Application No. 07250615.7, 11 pages (Sep. 19, 2007).

EP, Partial European Search Report, European Application No. 07250599.3, 4 pages (May 29, 2007).

EP, European Search Report, European Application No. 07250599.3, 11 pages (Aug. 22, 2007).

EP, Examination Report, European Application No. 07250599.3, 3 pages (Apr. 27, 2009).

* cited by examiner

ENERGY-BASED MEDICAL TREATMENT SYSTEM AND METHOD

FIELD OF THE INVENTION

The present invention is related generally to medical treatment systems and methods, and more particularly to an energy-based medical treatment system and to an energy-based medical treatment method.

BACKGROUND OF THE INVENTION

Energy-based medical treatment systems are known which include a clamp coagulator in the form of an ultrasonic surgical shears having an ultrasonic surgical blade, a clamping arm operable to open and close toward the blade, a tissue pad attached to the clamping arm, and a device for exerting a clamping force on the clamping arm which creates a clamping pressure on a blood vessel which is positioned between the clamping surface area of the tissue pad and the blade. The result of the ultrasonically-vibrating ultrasonic surgical blade and the clamping pressure on the blood vessel is a coaptation of the blood vessel (a bringing together of the walls of the blood vessel), a transection (a cutting) of the coaptated blood vessel, and a coagulation (a sealing) of the coaptated cut ends of the blood vessel. Energy-based medical treatment systems in the form of RF (radio-frequency) clamp coagulators are also known.

Still, scientists and engineers continue to seek improved energy-based medical treatment systems and improved energy-based medical treatment methods.

SUMMARY OF THE INVENTION

A method of the invention is for medical treatment and includes steps a) through g). Step a) includes obtaining an energy-based clamp coagulator. Step b) includes applying a clamping force to patient tissue using the energy-based clamp coagulator. Step c) includes beginning coagulating the patient tissue using the energy-based clamp coagulator. Step d) includes determining the clamping force. Step e) includes measuring the acoustic impedance of the patient tissue. Step f) includes compensating the measured acoustic impedance of the patient tissue for clamp pressure using at least the determined clamping force. Step g) includes monitoring the coagulation of the patient tissue using at least the compensated measured acoustic impedance.

A first embodiment of the invention is for an energy-based medical treatment system including an energy-based clamp coagulator, an acoustic-impedance measurer, and a force measurer. The energy-based clamp coagulator is adapted to clamp patient tissue. The acoustic-impedance measurer is operatively connected to the energy-based clamp coagulator to measure an acoustic impedance of the clamped patient tissue. The force measurer is operatively connected to the energy-based clamp coagulator to measure a clamp force on the clamped patient tissue.

A second embodiment of the invention is for an energy-based medical treatment system including an energy-based clamp coagulator having two clamping members adapted to coagulate patient tissue clamped between the two clamping members, wherein the two clamping members include, or are adapted to function as, electrical-impedance-measuring electrodes for measuring an electrical impedance of the clamped patient tissue.

A third embodiment of the invention is for an energy-based medical treatment system including an energy-based clamp coagulator having two clamping members adapted to coagulate patient tissue clamped between the two clamping members, wherein at least one of the two clamping members includes, or is adapted to function as, a temperature sensor for measuring a temperature of the clamped patient tissue.

Several benefits and advantages are obtained from one or more of the method and the embodiments of the invention. In one example, monitoring the coagulation of patient tissue allows a controller to turn off, or to activate an indicator which indicates to a user to turn off, the energy-based clamp coagulator when tissue coagulation is completed without the coagulation progressing to non-target tissue and without the energy further desiccating or damaging the target tissue.

The present invention has, without limitation, application with straight or curved ultrasonic surgical blades (when the energy used is ultrasound) and further in hand-activated instruments as well as in robotic-assisted instruments.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
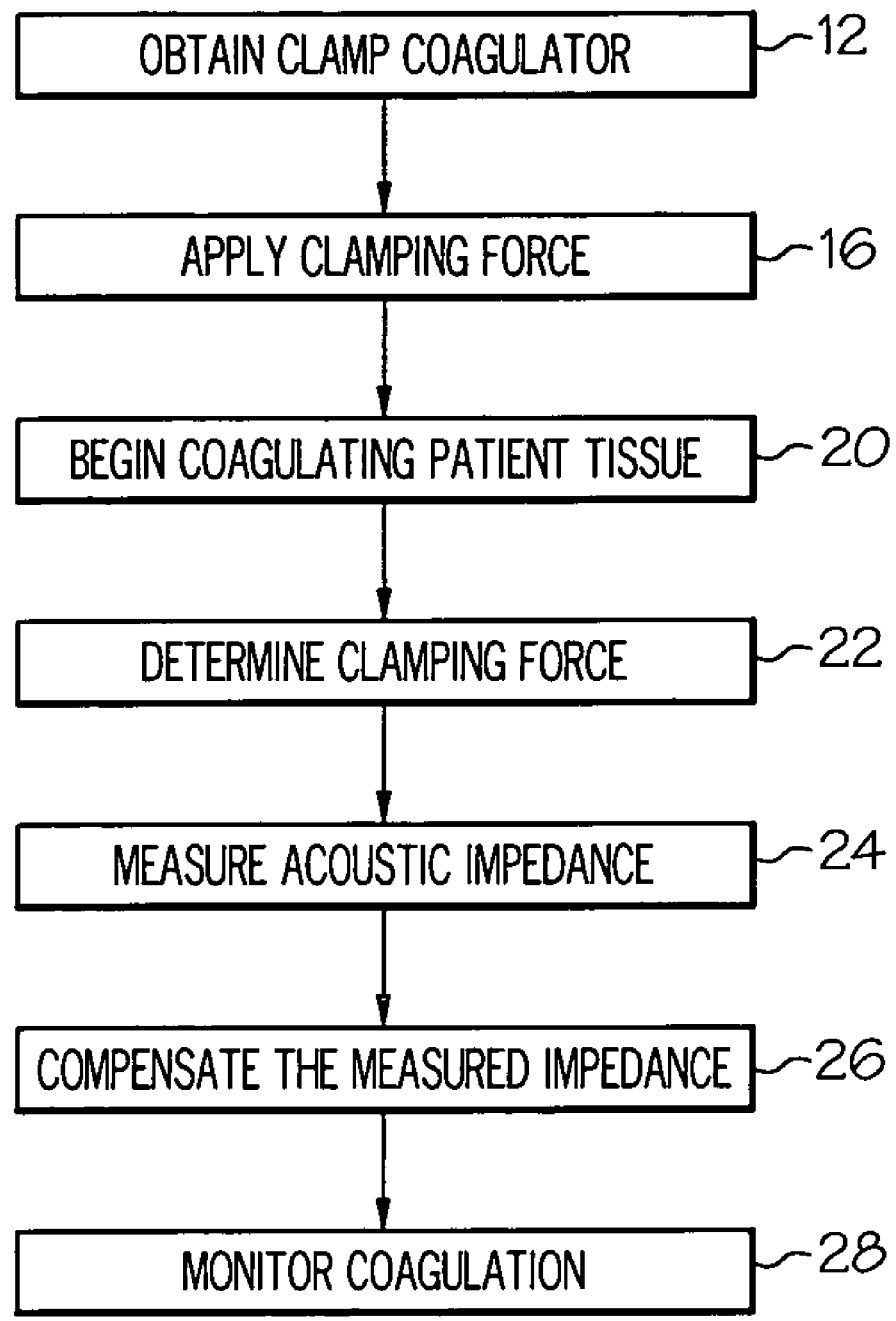
FIG. 1 is a block diagram of a method of the invention.
Figure 2:
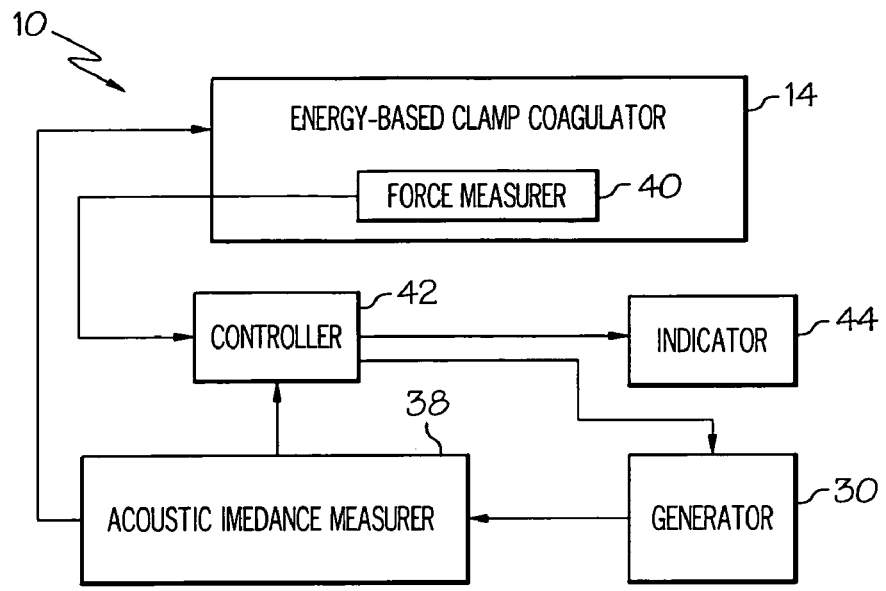
FIG. 2 is a schematic block diagram of a first embodiment of an energy-based medical treatment system of the invention including an energy-based clamp coagulator, an acoustic-impedance measurer, and a force measurer.
Figure 3:
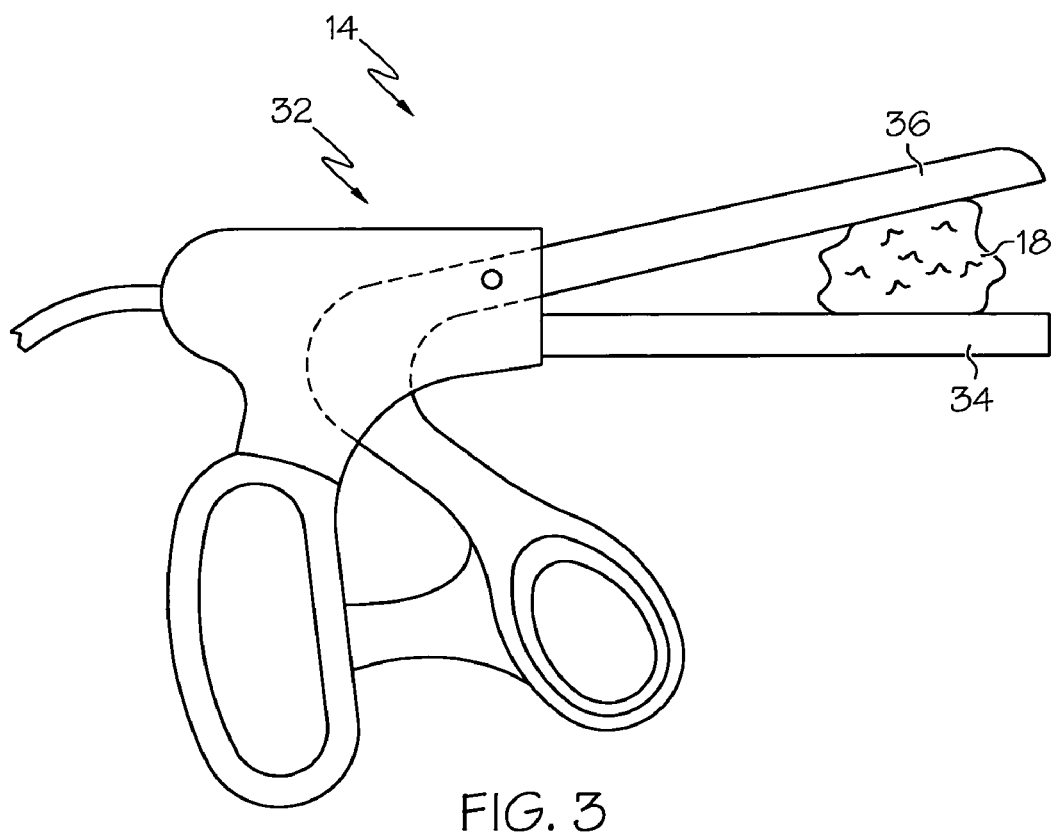
FIG. 3 is a schematic side elevational view of the energy-based clamp coagulator of FIG. 2.

Referring now to the Figures, in which like numerals indicate like elements, FIG. 1 illustrates a method of the invention with FIGS. 2-3 illustrating an embodiment of an energy-based medical treatment system 10 as one example of apparatus for carrying out the method. The method is for medical treatment and includes steps a) through g). Step a) is labeled as "Obtain Clamp Coagulator" in block 12 of FIG. 1. Step a)

includes obtaining an energy-based clamp coagulator 14. Step b) is labeled as "Apply Clamping Force" in block 16 of FIG. 1. Step b) includes applying a clamping force to patient tissue 18 using the energy-based clamp coagulator 14. Step c) is labeled as "Begin Coagulating Patient Tissue" in block 20 of FIG. 1. Step c) includes beginning coagulating the patient tissue 18 using the energy-based clamp coagulator 14. Step d) is labeled as "Determine Clamping Force" in block 22 of FIG. 1. Step d) includes determining the clamping force. Step e) is labeled as "Measure Acoustic Impedance" in block 24 of FIG. 1. Step e) includes measuring the acoustic impedance of the patient tissue 18. Step f) is labeled as "Compensate The Measured Impedance" in block 26 of FIG. 1. Step f) includes compensating the measured acoustic impedance of the patient tissue 18 for clamp pressure using at least the determined clamping force. Step g) is labeled as "Monitor Coagulation" in block 28 of FIG. 1. Step g) includes monitoring the coagulation of the patient tissue 18 using at least the compensated measured acoustic impedance.

In one illustration of the method of the invention, the energy-based clamp coagulator 14 is powered by an output power of a generator 30. In this illustration, the method also includes the step of adjusting the output power based on the monitored coagulation of the patient tissue 18. In one variation, the output power is adjusted lower as the monitored coagulation nears completion, and the generator 30 is turned off when the monitored coagulation reaches completion. In a different illustration, the method also includes the step of notifying (such as by visual and/or audio and/or other cues) a user of the energy-based clamp coagulator 14 of the monitored coagulation of the patient tissue 18 (such as notifying when coagulation is completed so the user can turn off power to the energy-based clamp coagulator 14).

In one application of the method of the invention, the energy-based clamp coagulator 14 is an ultrasonic surgical shears 32 having an ultrasonic blade 34 and a clamp arm 36 (whose tissue pad has been omitted from FIG. 1 for clarity). In a different application, not shown, the energy-based clamp coagulator is an RF (radio-frequency) clamp coagulator having a monopolar electrode or bipolar electrode. In one variation, the RF clamp coagulator has two clamping members each supporting, or adapted to function as, a bipolar electrode for electric current to flow between the two clamping members.

A first embodiment of the invention is for an energy-based medical treatment system 10 and is shown in FIGS. 2-3. The energy-based medical treatment system 10 includes an energy-based clamp coagulator 14, an acoustic-impedance measurer 38, and a force measurer 40. The energy-based clamp coagulator 14 is adapted to clamp patient tissue 18. The acoustic-impedance measurer 38 is operatively connected to the energy-based clamp coagulator 14 to measure an acoustic impedance of the clamped patient tissue 18. The force measurer 40 is operatively connected to the energy-based clamp coagulator 14 to measure a clamp force on the clamped patient tissue 18.

In one implementation of the embodiment of FIGS. 2-3, the acoustic-impedance measurer 38 includes circuitry (not shown) which determines, during the medical treatment, the output power of the generator 30, which determines the current flowing from the generator 30, and which divides the determined output power by the square of the determined current since acoustic impedance is seen as an electrical quantity by the generator 30. In the same or a different implementation, the force measurer 40 includes a force transducer (not shown) which measures a force (a manually applied force for a manually-driven clamp arm or a motor applied force [wherein a torque is considered a rotational force] for a motor-driven clamp arm) exerted by a user or a motor on the clamping mechanism of the energy-based clamp coagulator 14 for the energy-based clamp coagulator 14 to apply a clamp force on the patient tissue 18, and includes circuitry (not shown) which converts the measured manual or motor force to a measured clamp force. Other implementations of acoustic-impedance measurers and force measurers are left to those skilled in the art.

In one enablement of the embodiment of FIGS. 2-3, the energy-based medical treatment system 10 also includes a controller 42 which compensates (i.e., corrects) the measurement of the acoustic impedance of the patient tissue 18 for clamp pressure using at least the measured clamp force. It is noted that the measured acoustic impedance increases with increasing clamp force, and such compensation of the measurement of the acoustic impedance for clamp pressure can be experimentally and/or mathematically determined by those skilled in the art and implemented by a mathematical table, a software algorithm, and/or circuitry which yields a value of the compensated acoustic impedance measurement for a value of the measured acoustic impedance and a value for the measured clamp force.

In one variation of the above-described enablement, the controller 42 also monitors the coagulation (i.e., the degree or state of coagulation) of the patient tissue 18 using at least the compensated measured acoustic impedance. In one employment, when the compensated measured acoustic impedance reaches an experimentally and/or mathematically determined upper limit, or when the shape of the impedance versus time graph reaches some predetermined shape, the coagulation is considered to be completed. In a first arrangement, the controller 42 controls a power output of a generator 30 based on the monitored coagulation of the patient tissue 18, wherein the power output powers the energy-based clamp coagulator 14. In a second arrangement, the controller 42 controls a visual and/or audio indicator 44 (which, in one example, emits a light or a beep) which indicates, to a user of the energy-based clamp coagulator 14, the monitored coagulation of the patient tissue 18.

In one deployment of the embodiment of FIGS. 2-3, the energy-based clamp coagulator 14 is an ultrasonic surgical shears 32 having an ultrasonic blade 34 and a clamp arm 36. In one variation, the force measurer 40 is adapted to measure the force applied to the clamp arm 36. In a different deployment, not shown, the energy-based clamp coagulator is an RF (radio-frequency) clamp coagulator having a monopolar electrode or bipolar electrode.

Figure 4:
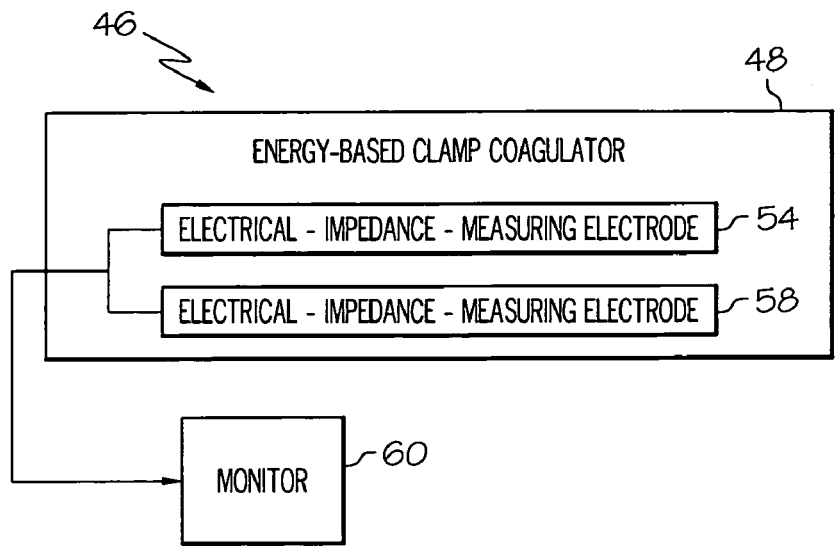
FIG. 4 is a schematic block diagram of a second embodiment of an energy-based medical treatment system of the invention including an energy-based clamp coagulator having two clamping members which include, or are adapted to function as, electrical-impedance-measuring electrodes.
Figure 5:
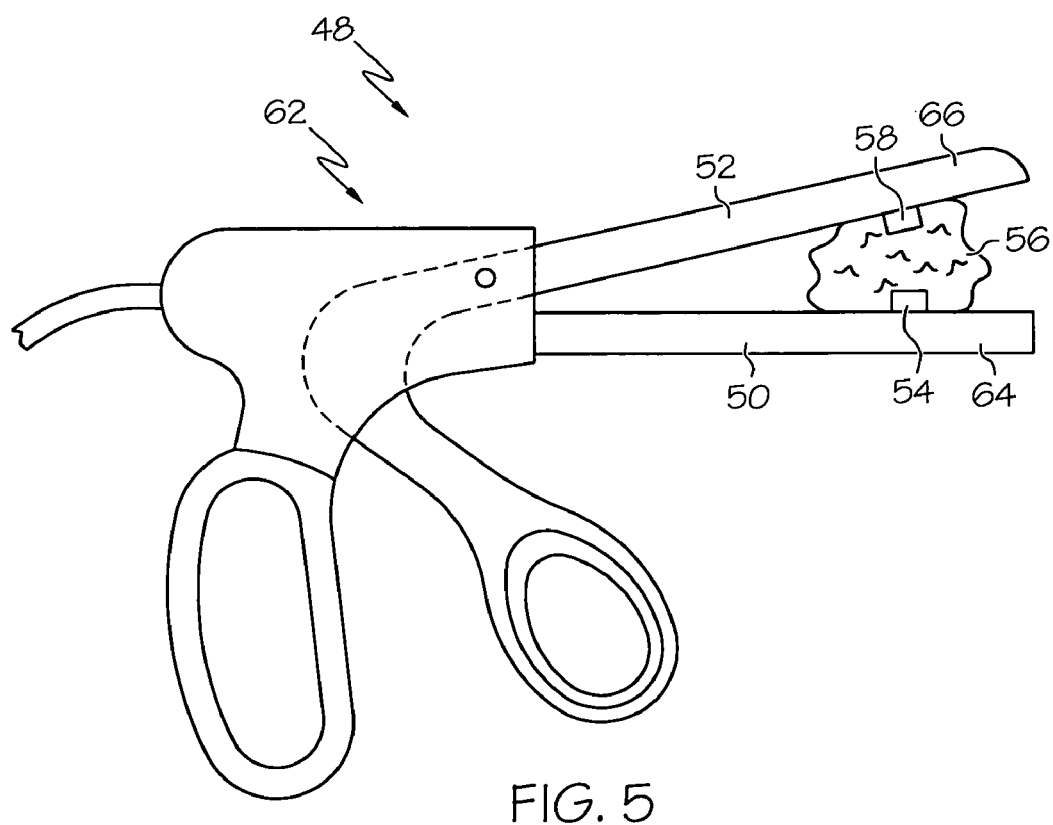
FIG. 5 is a schematic side elevational view of the energy-based clamp coagulator of FIG. 4.

A second embodiment of the invention is for an energy-based medical treatment system 46 and is shown in FIGS. 4-5. The energy-based medical treatment system 46 includes an energy-based clamp coagulator 48. The energy-based clamp coagulator 48 has two clamping members 50 and 52, wherein at least one 50 of the two clamping members 50 and 52 includes, or is adapted to function as, an electrical-impedance-measuring electrode 54 for measuring an electrical impedance of the clamped patient tissue 56.

In one example of the embodiment of FIGS. 4-5, the other 52 of the two clamping members 50 and 52 also includes an electrical-impedance-measuring electrode 58, wherein a small sensing current passes between the two electrodes 54 and 58 and is used to determine the electrical impedance of the clamped patient tissue 56, as is within the skill of the artisan. In another example, not shown, a clamping member has two electrodes and a small sensing current passes between the two electrodes.

In one enablement of the embodiment of FIGS. 4-5, the energy-based medical treatment system 46 includes a monitor 60 (such as a controller similar to the controller 42 and with the added controlling functions of the controller 42) which monitors the coagulation (i.e., the degree or state of coagulation) of the clamped patient tissue 56 using at least the measured electrical impedance of the clamped patient tissue 56 obtained from using at least the electrical-impedance-measuring electrode 54. In one variation, the electrical impedance of the patient tissue 56 is used as a measure of the degree of coagulation. As the patient tissue 54 is coagulating from being heated by the energy-based clamp coagulator 48, the ability of the coagulating patient tissue 54 to conduct current decreases which is reflected by increases in the electrical impedance of the patient tissue 54. In a different variation, the shape of the electrical impedance versus time curve is used to determine the coagulation state of the tissue.

In one deployment of the embodiment of FIGS. 4-5, the energy-based clamp coagulator 46 is an ultrasonic surgical shears 62 having an ultrasonic blade 64 (powered by a generator, not shown) and a clamp arm 66. It is noted that, in this deployment, the one 50 of the two clamping members 50 and 52 includes the ultrasonic blade 64 and the other 52 of the two clamping member 50 and 52 includes the clamp arm 66. In a different deployment, not shown, the energy-based clamp coagulator is an RF (radio-frequency) clamp coagulator having a monopolar electrode or bipolar electrode.

Figure 6:
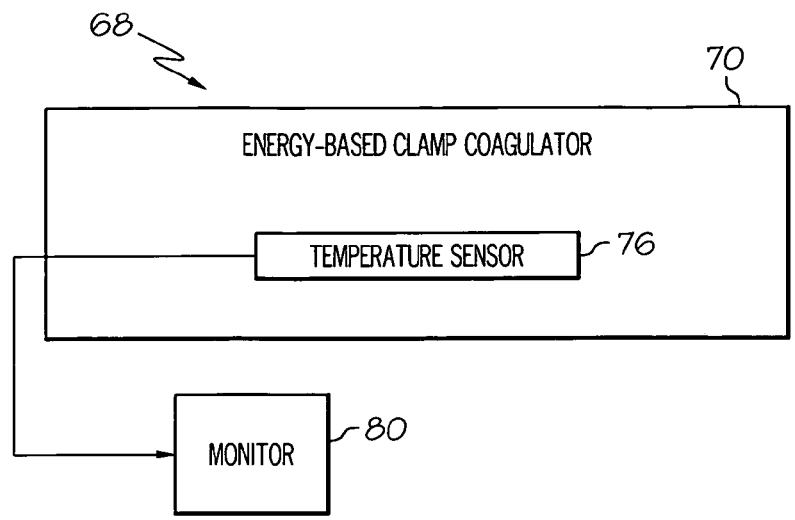
FIG. 6 is a schematic block diagram of a third embodiment of an energy-based medical treatment system of the invention including an energy-based clamp coagulator having two clamping members at least one of which includes, or is adapted to function as, a temperature sensor.
Figure 7:
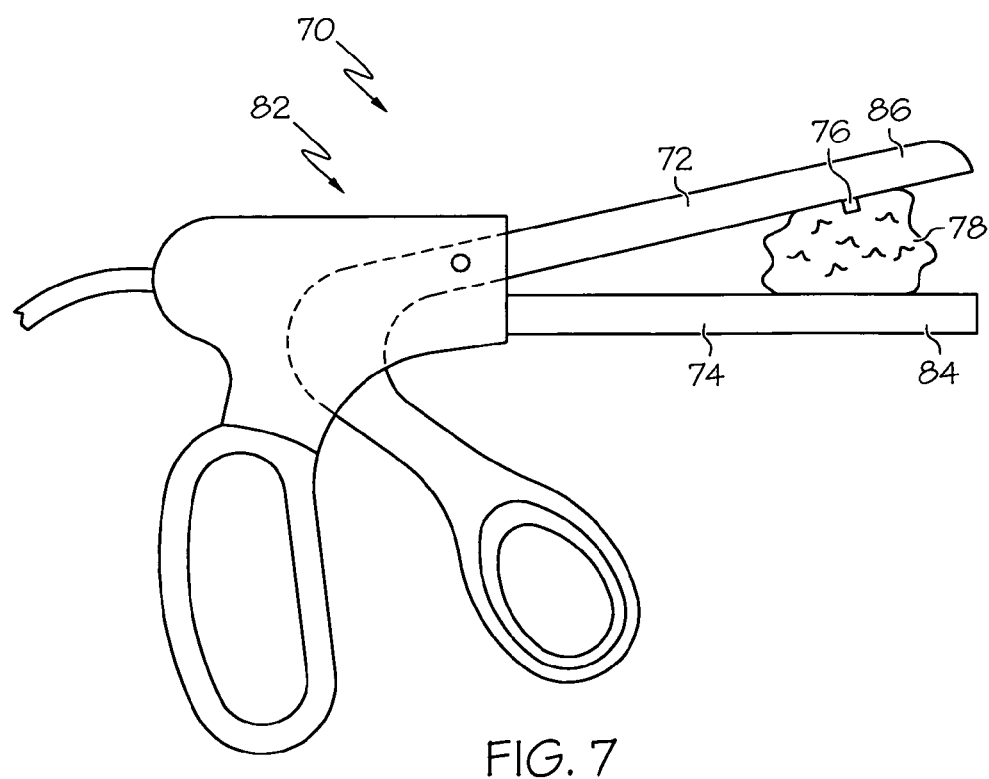
FIG. 7 is a schematic side elevational view of the energy-based clamp coagulator of FIG. 6.

A third embodiment of the invention is for an energy-based medical treatment system 68 and is shown in FIGS. 6-7. The energy-based medical treatment system 68 includes an energy-based clamp coagulator 70. The energy-based clamp coagulator 70 has two clamping members 72 and 74, wherein at least one 72 of the two clamping members 72 and 74 includes, or is adapted to function as, a temperature sensor 76 for measuring a temperature of the clamped patient tissue 78.

In one enablement of the embodiment of FIGS. 6-7, the energy-based medical treatment system 68 includes a monitor 80 (such as a controller similar to the controller 42 and with the added controlling functions of the controller 42) which monitors the coagulation (i.e., the degree or state of coagulation) of the clamped patient tissue 78 using at least the measured temperature of the clamped patient tissue 78 obtained from using at least the temperature sensor 76. It is noted that the temperature of the patient tissue 78 is a measure of the degree of coagulation. As the patient tissue 78 is coagulating from being heated by the energy-based clamp coagulator 70, the tissue is first denatured and coagulated, after which the tissue becomes desiccated and the temperature of the tissue increases.

In one deployment of the embodiment of FIGS. 6-7, the energy-based clamp coagulator 68 is an ultrasonic surgical shears 82 having an ultrasonic blade 84 (powered by a generator, not shown) and a clamp arm 86. It is noted that, in this deployment, the one 72 of the two clamping members 72 and 74 includes the clamp arm 86 and the other 74 of the two clamping member 72 and 74 includes the ultrasonic blade 84. In a different deployment, not shown, the energy-based clamp coagulator is an RF (radio-frequency) clamp coagulator having a monopolar electrode or bipolar electrode.

Several benefits and advantages are obtained from one or more of the method and the embodiments of the invention. In one example, monitoring the coagulation of patient tissue allows a controller to turn off, or to activate an indicator which indicates to a user to turn off, the energy-based clamp coagulator when tissue coagulation is completed without the coagulation progressing to non-target tissue and without the energy further desiccating or damaging the target tissue.

While the present invention has been illustrated by a description of several embodiments and a method, it is not the intention of the applicants to restrict or limit the spirit and scope of the appended claims to such detail. Numerous other variations, changes, and substitutions will occur to those skilled in the art without departing from the scope of the invention. For instance, the energy-based medical treatment systems of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An energy-based medical treatment system comprising:
   a) an energy-based clamp coagulator adapted to clamp patient tissue;
   b) an acoustic-impedance measurer operatively connected to the energy-based clamp coagulator to measure an acoustic impedance of the clamped patient tissue;
   c) a force measurer operatively connected to the energy-based clamp coagulator to measure a clamp force on the clamped patient tissue; and
   d) a controller which compensates the measured acoustic impedance of the patient tissue for clamp pressure using at least the measured clamp force.

2. The energy-based medical treatment system of claim 1, wherein the controller also monitors a coagulation of the patient tissue using at least the compensated measured acoustic impedance.

3. The energy-based medical treatment system of claim 2, wherein the controller controls a power output of a generator based on the monitored coagulation of the patient tissue, wherein the power output powers the energy-based clamp coagulator.

4. The energy-based medical treatment system of claim 3, wherein the controlled power output is adjusted lower by the controller as the monitored coagulation of the patient tissue nears completion.

5. The energy-based medical treatment system of claim 3, wherein the controlled power output is turned off by the controller when the monitored coagulation of the patient tissue is completed.

6. The energy-based medical treatment system of claim 2, wherein the controller controls a visual and/or audio indicator which indicates, to a user of the energy-based clamp coagulator, the monitored coagulation of the patient tissue.

7. The energy-based medical treatment system of claim 6, wherein the energy-based clamp coagulator is an ultrasonic surgical shears having an ultrasonic blade and a clamp arm.

8. The energy-based medical treatment system of claim 7, wherein the force measurer is adapted to measure a force applied to the clamp arm.

9. An energy-based medical treatment system comprising:
   a) an energy-based clamp coagulator adapted to clamp patient tissue;
   b) an acoustic-impedance measurer operatively connected to the energy-based clamp coagulator, the acoustic-impedance measurer determining a value of acoustic impedance based on a generator output power;
   c) a force measurer operatively connected to the energy-based clamp coagulator, the force measurer determining a value of clamping force based on a force transducer output; and
   d) a controller generating a value of compensated acoustic impedance from the value of acoustic impedance based on at least the value of clamping force, wherein the value of compensated acoustic impedance is corrected to a value less than the value of acoustic impedance with increasing values of clamping force.

10. The energy-based medical treatment system of claim 9, wherein the controller monitors a coagulation of the patient tissue using at least the value of compensated acoustic impedance.

11. The energy-based medical treatment system of claim 10, wherein the controller controls the generator output power based on the monitored coagulation of the patient tissue, wherein the generator output power powers the energy-based clamp coagulator.

12. The energy-based medical treatment system of claim 11 wherein the controller reduces generator power output as the value of compensated acoustic impedance nears a predetermined upper limit.

13. The energy-based medical treatment system of claim 11 wherein the controller stops generator power output when the value of compensated acoustic impedance reaches a predetermined upper limit.

14. The energy-based medical treatment system of claim 11 wherein the controller reduces generator power output as the state of an acoustic impedance versus time relationship nears a predetermined state.

15. The energy-based medical treatment system of claim 11 wherein the controller stops generator power output as the state of an acoustic impedance versus time relationship reaches a predetermined state.

16. The energy-based medical treatment system of claim 11, wherein the controller controls a visual and/or audio indicator which indicates, to a user of the energy-based clamp coagulator, the monitored coagulation of the patient tissue.

17. The energy-based medical treatment system of claim 16, wherein the energy-based clamp coagulator is an ultrasonic surgical shears having an ultrasonic blade and a clamp arm.

18. The energy-based medical treatment system of claim 17, wherein the force transducer is adapted to measure a force applied to the clamp arm.

* * * * *